United States Patent [19]
Neher

[11] Patent Number: 4,625,677
[45] Date of Patent: Dec. 2, 1986

[54] APPARATUS FOR COATING AND POLISHING A MICROPIPETTE

[75] Inventor: Erwin Neher, Edigehausen, Fed. Rep. of Germany

[73] Assignee: Max-Planck-Gesellschaft zur Foerderung der Wissenschaften e.V., Fed. Rep. of Germany

[21] Appl. No.: 737,192

[22] Filed: May 23, 1985

[51] Int. Cl.$^4$ .............................................. B05C 11/00
[52] U.S. Cl. ..................................... 118/713; 65/284; 118/66; 118/643; 350/244
[58] Field of Search .......................... 118/713, 66, 643; 427/8, 284; 350/243, 244; 65/162, 284

[56] References Cited

U.S. PATENT DOCUMENTS 4,262,426 4/1981 Miyazaki ............................... 33/189
4,510,442 4/1985 Neher ................................. 324/99 R

OTHER PUBLICATIONS

Hawley, G. G., "The Condensed Chemical Dictionary", Ninth Edition, New York, Van Nostrand Reinhold Company, 1977, pp. 832, 949.
Hamill, O. P. et al., "Improved Patch-Clamp Techniques ... Patches", *Pflugers Archiv-European Journal of Physiology*, 391 (1981), p.p. 85-100.
Corey, D. P. and Stevens, C. F., "Science and Technology of Patch-Recording Electrodes", In: Sakmann, B. and Neher, E. (eds), *Single Channel Recording* (New York, Plenum Press, 1983), pp. 53-68.

*Primary Examiner*—Evan K. Lawrence
*Attorney, Agent, or Firm*—Henry C. Nields

[57] ABSTRACT

An apparatus for coating and polishing a micropipette for patch recording comprises an inverse microscope having a stage for supporting a micropipette to be processed, and a pair of objectives of relatively low and relatively high magnification, respectively, which are adapted to be selectively placed into the optical path of the microscope. An air gun is positioned to supply an air jet to a pipette supported on the stage, said gun comprising heating means for selectively producing a hot and a cold air jet. An attchment comprising an electricially heatable filament is associated to the objective of relatively high magnification. The micropipette is positioned and coated under observation with the aid of the objective of low magnification and then the coating is cured by applying the hot air jet. Subsequently, the tip of the pipette is polished by the heated filament under observation with the aid of the objective of high magnification. These steps may be performed without the necessity of changing or readjusting the position of the micropipette between these two processing steps.

10 Claims, 9 Drawing Figures

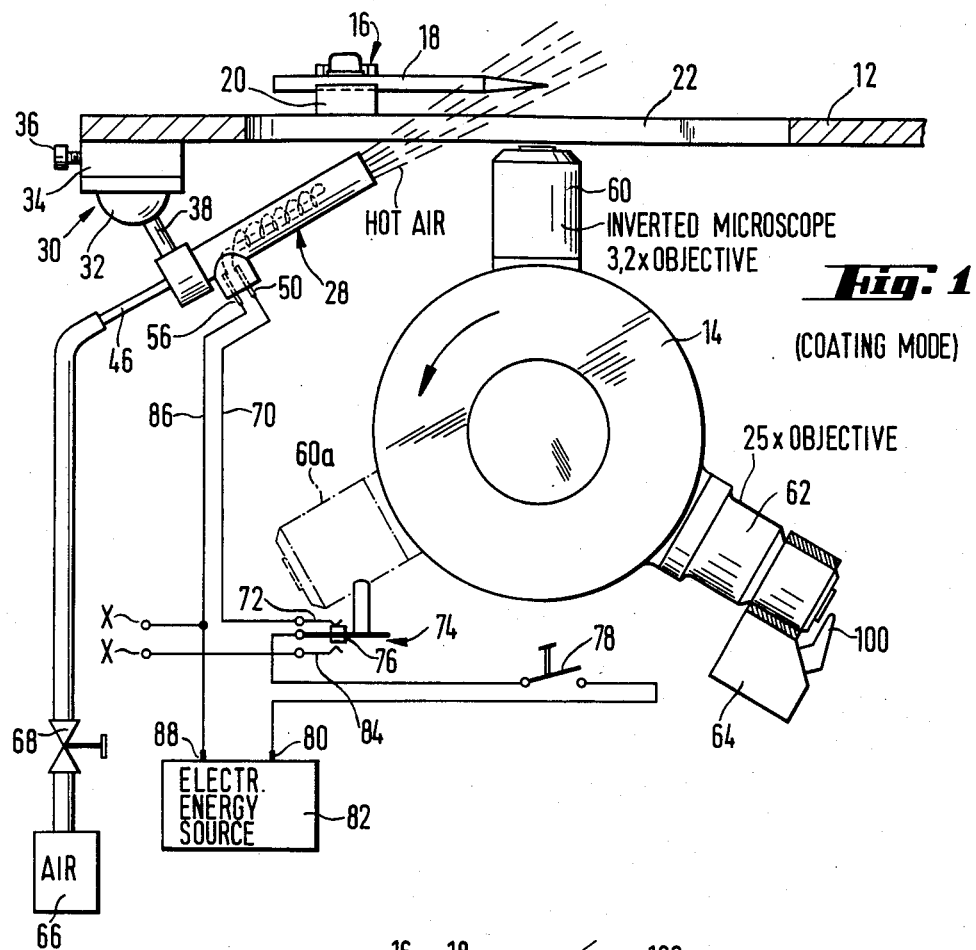
Fig. 1 (COATING MODE)
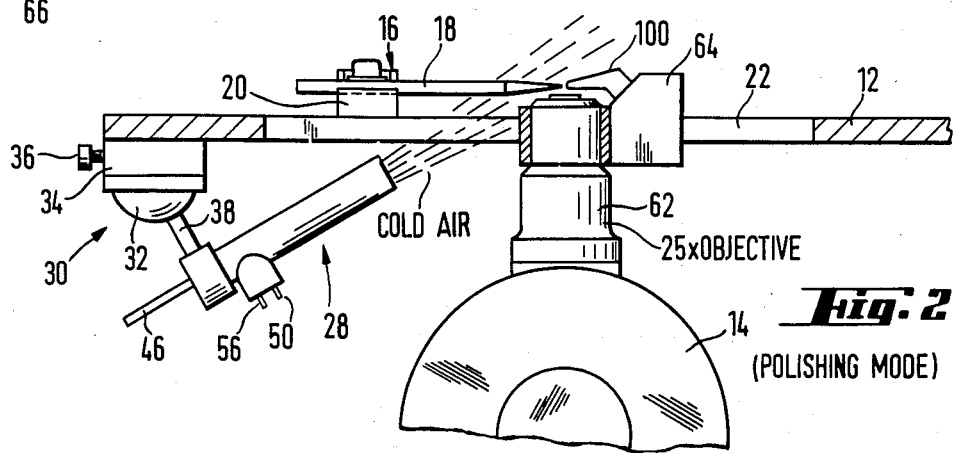
Fig. 2 (POLISHING MODE)

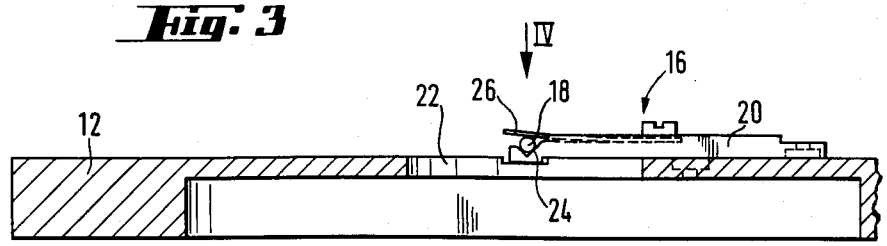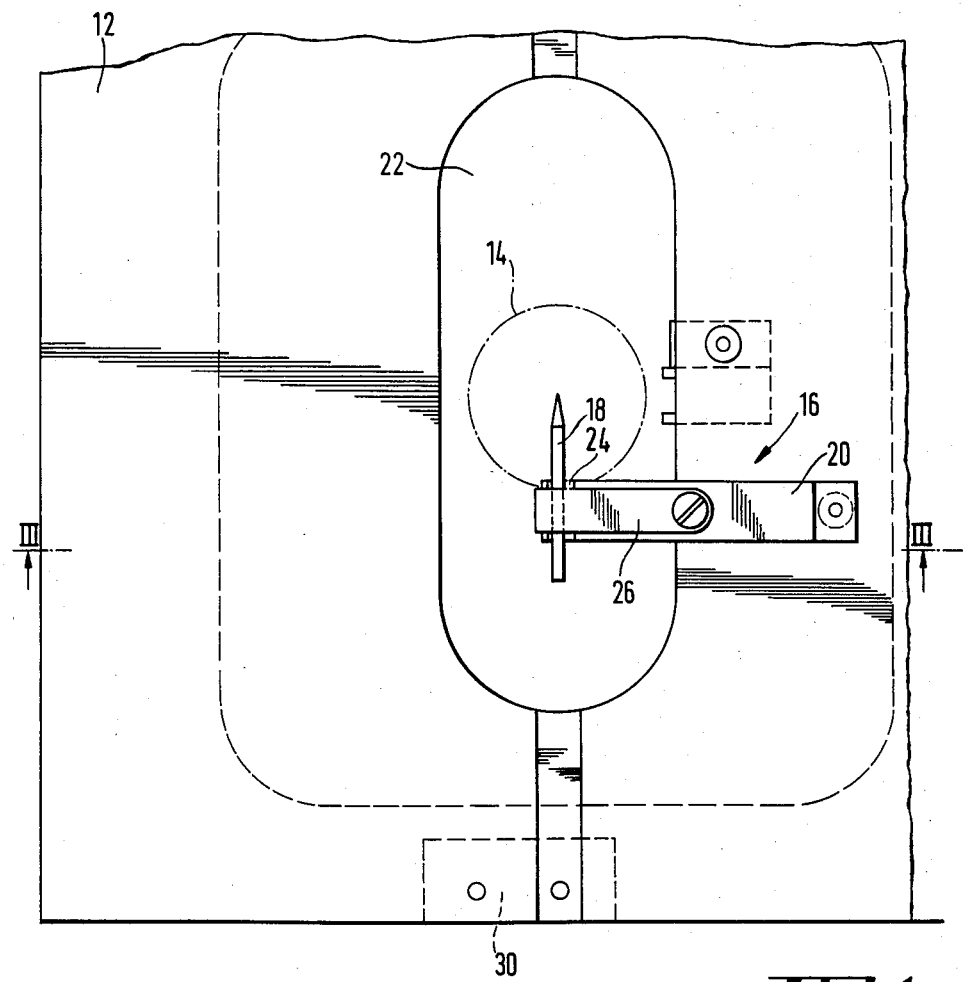

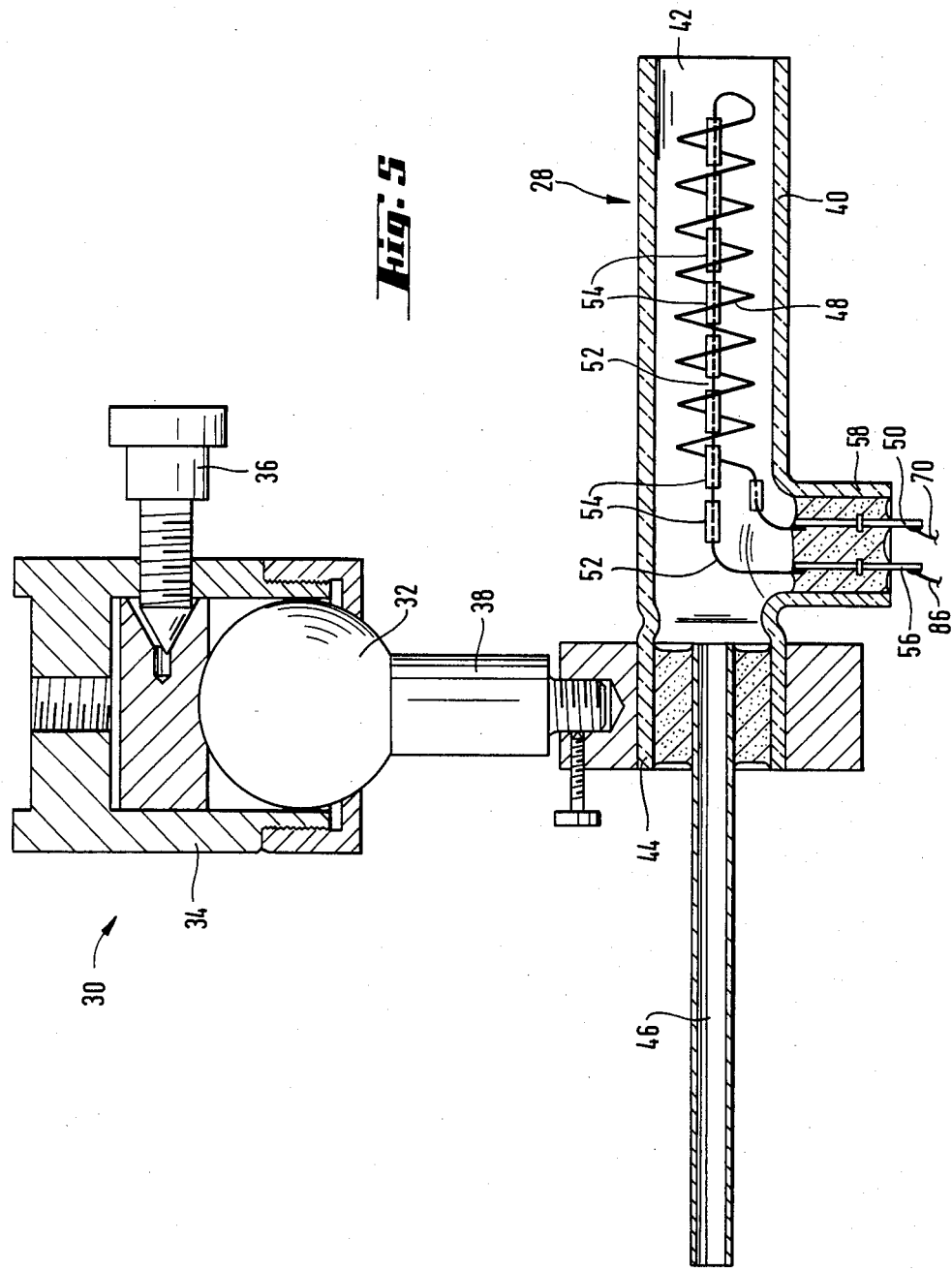

APPARATUS FOR COATING AND POLISHING A MICROPIPETTE

The present invention relates to patch-recording and more specifically to apparatus for coating and polishing micropipettes for patch recording of cell membrane currents.

BACKGROUND OF THE INVENTION

Patch-clamp techniques for high-resolution current recording from cells and cell-free membrane patches are well established in the biological art and described i.e. in "Pfluegers Archiv"/European Journal of Physiology 391 (1981) pages 85–100. The science and technology of patch-recording electrodes is described in "Single Channel Recording" (B. Sakmann and E. Neher, eds.), Plenum Press, New York and London (1983), pages 53 to 68. A copy of these publications is submitted with this application. A measuring system for exceedingly weak currents useful for patch recording is described in U.S. Pat. No. 4,510,442 issued Apr. 9, 1985 and incorporated by reference.

Patch pipettes are generally made by a three-stage process: Pulling a pipette, coating of its shank with a silicone resin, such as "Sylgard"(trademark of Dow Corning Corp.), and heat polishing of the pipette tip. The present invention relates to said second and third process steps.

The "Sylgard" coating is employed for the purpose of reducing the pipette-bath capacitance and to form a hydrophobic surface. In the known process, this step is performed by using a coating jig comprising a clamp for positioning the pipette, and a nichrome heating coil surrounding the shank of the micropipette and used to cure the coating which had been previously applied. Generally, the coating and the control of the curing are effected with the aid of a microscope with a low power objective.

A peculiarity of uncured "Sylgard" is that a very fine film of this resin tends to creep along the glass surface of the pipette for several millimeters, e.g. to the electrode tip. Since seals of very high resistance as desired for patch recording form only to clean glass, this film must be removed what is effected by burning it off in the third, the heat polishing step. Polishing the pipette tip also prevents damage to the membrane by sharp tip edges.

Polishing is usually done on the stage of a compound microscope under observation with a relatively high power, long working distance objective. The polishing assembly includes a V-shaped, electrically heatable filament and means comprising a tube to direct an air stream to the filament. The air stream is used to generate a steep thermal gradient which confines the polishing action to the very tip of the electrode.

SUMMARY OF THE INVENTION

The known method of coating and heat polishing micropipettes is slow and cumbersome, since the micropipette must be individually positioned and the microscope must be individually focussed in both the coating and the polishing steps.

The present invention solves these problems by providing an apparatus for both coating and polishing a micropipette. A preferred embodiment of the apparatus comprises an inverted microscope having a stage or table and relatively low power and relatively high power objectives which are adapted to be selectively moved into operative relationship with respect to the stage. A fixture for supporting and positionong a micropipette to be coated and polished is mounted on the top of the stage. An air gun, which is adapted to deliver selectively hot and cold air jets is mounted below the stage. A polishing fixture comprising an electrically heatable filament is mounted on the high power objective so that the filament is in close proximity of the tip of the pipette to be processed, when the high power objective is in it operative position.

Further objects, features and benefits of the invention will become apparent when reading the following detailed description of a preferred embodiment of the invention.

BRIEF DESCRIPTION OF THE DRAWINGS

FIG. 1 is a simplified, diagrammatic view, partially in section, of a preferred embodiment of the invention shown in the coating mode;

FIG. 2 is a partial view of the apparatus of FIG. 1 in the polishing mode;

FIG. 3 and 4 are sectional side and plane views respectively, of a microscope stage or table;

FIG. 5 is a sectional side view of an air gun of the apparatus of FIGS. 1 and 2;

DESCRIPTION OF PREFERRED EMBODIMENT

Figure 6:
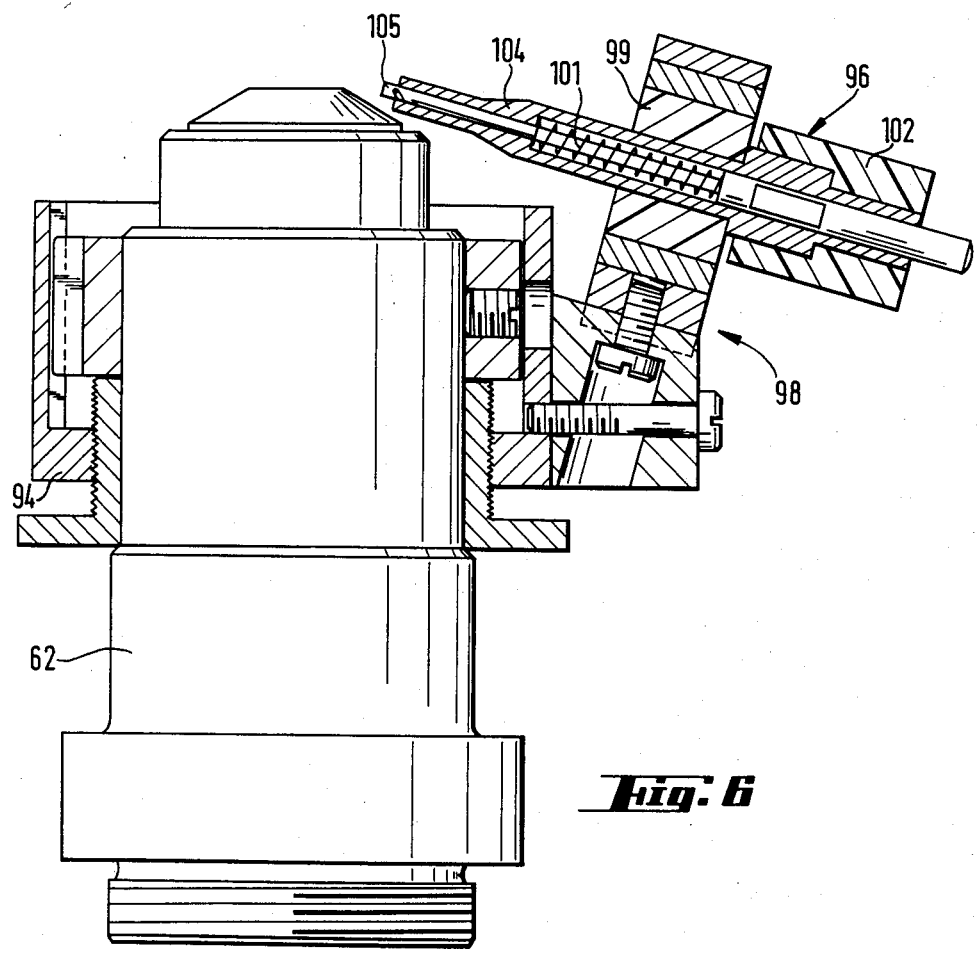
FIG. 6 is a side view, partially in section, of a high power objective of the apparatus of FIGS. 1 and 2 with a polishing attachment.

The apparatus according to the presently preferred embodiment of the invention is based on a so-called inverse or inverted microscope, e.g. Type IM sold by Carl Zeiss, Oberkochen, Fed. Rep. of Germany. An inverse microscope is an optical microscope, in which the objective system is below the stage and looking upwardly, so that an object positioned on the stage can be observed from below and is freely accessible from above.

Only a table or stage 12 and an objective revolver 14 are diagrammatically shown of the inverted microscope. The stage is provided with a conventional specimen positioner (not shown), which allows to position a specimen supported on the stage relative to the optical path of the microscope. A fixture 16 for supporting a micropipette 18 to be coated and polished is mounted on the top of the stage 12. As shown in more detail in FIGS. 3 and 4, the fixture 16 comprises a mounting block 20 which is adapted to have its position adjusted by the specimen positioner. The mounting block 20 protrudes in a cantilever fashion into aperture 22 of the stage 12 and has, adjacent to its free end, a groove 24 for receiving the micropipette 18. A leaf spring 26 is mounted on the mounting block 20 and extends over the groove 24 to hold the micropipette 18 in its position within the groove 24.

An air gun 28, which will be described in more detail with reference to FIG. 5, is supported by an universal joint mounting 30 below the stage 12, so that the nozzle of the air gun is pointed to the portion of the micropipette 18 protruding over the aperture 22.

The universal joint mounting shown in section in FIG. 5 comprises a ball member 32 seated in a housing 34 which is attached by screws (not shown) to the lower side of the stage 12. The position of the ball member 32 with respect to the housing 34 may be fixed after adjustment of the gun by means of a set screw 36.

The air gun 28 (FIG. 5) is mounted on a stem 38 protruding from the ball member 32 and comprises a tube 40 made of borosilicate glass and having a nozzle end 42 and a rear end 44. An air supply duct 46 is connected to the rear end. The tube 40 comprises an electrical heating element 48 which is formed by a coil of 250 micron diameter 90 Pt-10 Ir wire. A first end of the coil is connected to a first terminal 50 while the other end of the coil is integral with a return conductor portion 52 of the Pt-Ir-wire which extends along the axis of the wire coil and is insulated by quartz glass capillaries 54 and is connected to a second terminal 56. The terminls are fused into a T-branch portion 58 of the tube 40.

Referring again to FIG. 1, the objective revolver 14 of the inverted microscope is provided with a first, relatively low power objective 60 having e.g. a magnification of 3.2 x, and with a second, relatively high power objective 62 having e.g. a magnification of 25 x. The high power objective 62 is provided with a polishing fixture 64 which will be described in more detail with reference to FIG. 6.

The air supply duct 46 of the air gun 28 is connected to a pressurized air supply 66 by a valve 68. The terminal 50 of the air gun 28 is coupled through a line 70 to a first fixed contact 72 of a single pole—double throw microswitch 74 which has a movable contact 76 connected through a foot actuable switch 78 to a first terminal 80 of an electric energy source 82. A second fixed contact 84 of the micro switch is connected to one of two terminals x of the polishing fixture 64, the other terminal x being connected to a line 86 coupling the terminal 56 to a second terminal 88 of the energy source 82.

Figure 7:
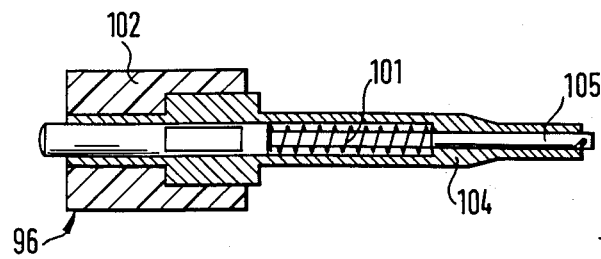
FIGS. 7 and 8 are sectional side and plane views, respectively, of a filament holder of the attachment shown in FIG. 6.
Figure 8:
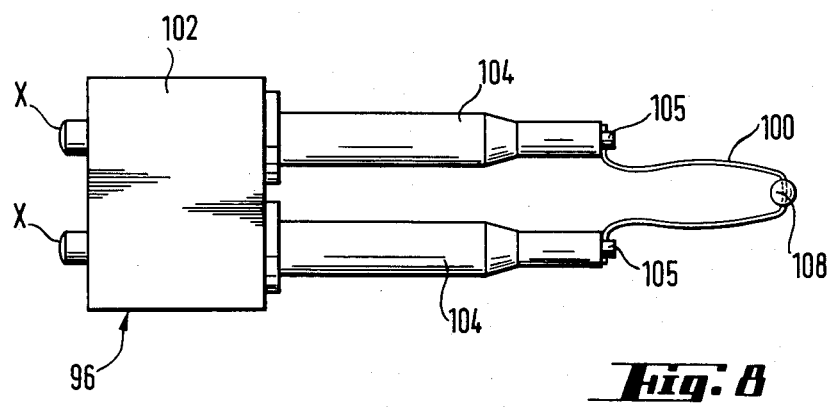
Figure 9:
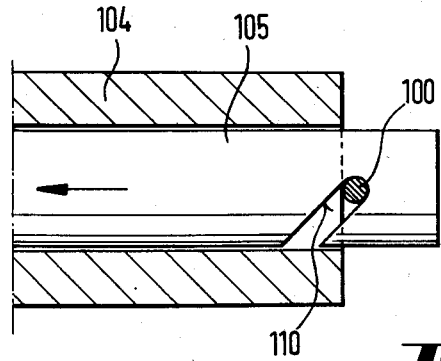
FIG. 9 is an enlarged side view, partially in section, of the front end of the filament holder of FIGS. 7 and 8.

Referring to FIGS. 6 to 9 the polishing fixture comprises mounting means 94 for mounting the polishing fixture on the barrel of the high power objective 62, further filment holder means, shown in more detail in FIGS. 7, 8 and 9, and adjusting means 98 coupling the filament holder 96 to the mounting means 94, such that the position of the tip of an electrically heatable filament 100 (FIG. 8) can be accurately adjusted with respect to the objective 62. More specifically, the adjusting means 98 is attached to the mounting means 94 by a screw forming a pivot for adjusting the filament transversely to the optical axis of the objective, and a spring biased sliding seat including a "Dynal" insulating bushing 99 and a pair of metal springs 101 each bearing on a stainless steel tube 104 of the filament holder 96. The springs 101 provide both mechanical clamping and electrical connection of the tubes 104. The filament holder 96 comprises a "Dynal" mounting block 102 supporting the pair of spaced tubes 104 which comprise rods 105 spring biased in inward direction as indicated by an arrow in FIG. 9. A transverse slot 110 is provided near the front end of each rod 105 to receive and clamp an end of the approximately V-shaped filament 100, the tip of which being coated with a glass bead 108. The filament 100 is a 100 μm Pt-Ir-wire.

OPERATION

Referring to FIGS. 1 and 2, a micropipette 18 to be coated and polished is positioned in the groove 24 of the mounting block 20. The low power objective 60 is moved into the optical path of the microscope. The objective 60 and the axial position of the micropipette 18 are adjusted so that the tip end of the micropipette is focussed in the center of the field of view of the microscope. Then, a coating of "Sylgard" is applied to the shank of the pipette as known in the art. Then, the valve 68 is opened to supply air to the air gun, and the foot switch 78 is actuated to energize the heating coil 48 via the contacts 76–72 of switch 74. Thus, a jet of hot air is applied to the "Sylgard"-coated micropipette 18 causing the "Sylgard" resin to cure. After the curing has been effected by the hot air jet, the foot switch 78 is released.

To set the apparatus for performing the polishing step, the high power objective 62 is moved into the optical path of the microscope by turning the objective revolver 14. In the embodiment shown, this brings the low power objective 60 in a position 60a shown in phantom lines in FIG. 1, in which the objective 60 actuates the switch 74 breaking the connection between contacts 72 and 76 and engaging contacts 76 and 84. Thus, the heating coil 78 is disconnected while the filament 100 is coupled into the circuit of the foot switch 78 and the energy source 82. The filament 100 which has been previously adjusted by means of adjusting means 98 (FIG. 6) is now in its operative position in relation to the tip of the micropipette 18 as diagrammatically shown in FIG. 2. Only minor adjustments to the position of the tip of the pipette by means of the microscope specimen positioner are necessary since the tip of the pipette is automatically in the focal plane and the field of view of the high power objective 62 because of the previous adjustment performed under low power magnification. For effecting the polishing, the foot switch 78 is again actuated which now causes to supply energy to the filament 100 which heats up and supplies the heat necessary for polishing the tip of the micropipette 18. The air gun 28 continues to deliver an air jet to the shank of the pipette for confining the polishing action to the very tip of the pipette. The air jet has now essentially room temperature because the filament 48 has been deenergized by switch 74. After the polishing has been effected under optical control by means of the high power objective 62, the foot switch 78 is released, the air supply is turned off by closing valve 68, and the now finished pipette 18 may be removed from the mounting block 18 and a new pipette to be processed may be inserted.

Various changes and modifications can be made to the above-described embodiment by those skilled in the art without departing from the scope of the invention which is defined by the attached claims. E.g. the microswitch 74 may be actuated by another part of the microscope or may be a manually actuated switch. Other suitable adjusting and mounting means may be used for supporting the air gun and the filament used for polishing. The polishing filament may be mounted on support and adjusting means which is essentially stationary with respect to the stage or the pipette mounting block. Other heating means, as an electrical heating element, as a heating coil, may be used for curing the polymer coating.

The heating means and the polishing means may be energized by different power sources selectively enabled by appropriate switch means, or they may be energized with different power levels from a single electrical power source, the output power level being selectively variable. Still other forms of this invention may become apparent to those skilled in the art upon reference to this disclosure and, thrrerefore, this invention shall be limited only by the scope of the appended claims.

I claim:

1. An apparatus for coating and heat polishing a micropipette having a shank portion and a tip end, said apparatus comprising
   (a) a microscope having a stage and an optical system, said optical system comprising a relatively low power objective and a relatively high power objective which are adapted to be positioned selectively in an operative relationship with respect to said stage,
   (b) first means for supporting and positioning a micropipette on said stage so that it can be coated and observed through either objective;
   (c) an air gun adapted to apply selectively hot or cold air jets to said pipette on said stage;
   (d) heat polishing means including an electrically heatable filament;
   (e) second means for supporting said filament, said second means being operatively associated to said high power objective to position said filament proximate to the tip end of said micropipette supported on said stage when said high power objective is moved in its operative position with respect to said stage.

2. The apparatus as claimed in claim 1 wherein said microscope is an inverted microscope with the objectives arranged below said stage and looking in upward direction when in the operative position.

3. The apparatus as claimed in claim 1 further comprising third means for mounting said air gun to said stage.

4. The apparatus as claimed in claim 1 wherein said second means comprises means for mounting and supporting said filament on said high power objective.

5. The apparatus as claimed in claim 1 wherein said air gun comprises an electrical heating element and said apparatus further comprises switch means for enabling the supply of electrical power to said heating element, when said low power objective is in its operative position, and for enabling the supply of electrical power to said filament when said high power objective is in its operative position.

6. The apparatus as claimed in claim 5, wherein said objectives are supported on a movable support and said switch means is adapted to be acutated upon movement of said support.

7. An apparatus for coating and heat polishing a micropipette having a shank portion and a tip end, said apparatus comprising
   (a) a microscope having a stage and an optical system, said optical system comprising a relatively low power objective and a relatively high power objective which are adapted to be positioned selectively in an operative relationship with respect to said stage,
   (b) first means for supporting and positioning a micropipette on said stage so that it can be observed through either objective;
   (c) heating means for applying heat to said micropipette supported on said stage;
   (d) heat polishing means including an electrically heatable filament;
   (e) second means for supporting said filament, said second means being adapted to position said filament proximate to the tip end of said micropipette supported on said stage.

8. The apparatus as claimed in claim 7 wherein said heating means comprises a hot air gun.

9. The apparatus as claimed in claim 7, wherein said heating means is coupled to said stage and said second means is coupled to said high power objective.

10. The apparatus as claimed in claim 7, wherein
    said microscope comprises a movable support on which said low and high power objectives are mounted, and said apparatus further comprises
    an electric power supply;
    switch means coupling said power supply selectively to said heating means or to said polishing means, and
    actuating means to actuate said switch means in respeonse to movement of said support.

* * * * *